(12) United States Patent
Mushtaque et al.

(10) Patent No.: US 11,579,433 B2
(45) Date of Patent: Feb. 14, 2023

(54) ENDOSCOPE AND LENS CLEANING DEVICE ASSEMBLY

(71) Applicant: Covidien LP, Mansfield, MA (US)

(72) Inventors: Syed Ahmed Mushtaque, Hyderabad (IN); Jeevan Maddur Shankar Setty, Bangalore (IN); Yogesh Kishor Vikharankar, Hyderabad (IN); Arifmohamad Mujawar, Sangli (IN)

(73) Assignee: Covidien LP, Mansfield, MA (US)

( * ) Notice: Subject to any disclaimer, the term of this patent is extended or adjusted under 35 U.S.C. 154(b) by 243 days.

(21) Appl. No.: 16/905,023

(22) Filed: Jun. 18, 2020

(65) Prior Publication Data
US 2021/0396986 A1    Dec. 23, 2021

(51) Int. Cl.
*G02B 23/16* (2006.01)
*G02B 23/24* (2006.01)
*A61B 1/12* (2006.01)

(52) U.S. Cl.
CPC .......... *G02B 23/2446* (2013.01); *A61B 1/121* (2013.01); *G02B 23/2476* (2013.01)

(58) Field of Classification Search
CPC .... G02B 21/00; G02B 21/0012; G02B 23/00; G02B 23/24; G02B 23/2446; G02B 23/2476; G02B 27/00; G02B 27/0006; G02B 23/16
USPC ................ 359/738–740, 507–514, 601–612
See application file for complete search history.

(56) References Cited

U.S. PATENT DOCUMENTS

| | | |
|---|---|---|
| 5,295,952 A | 3/1994 | Pietrafitta |
| 5,382,297 A | 1/1995 | Valentine et al. |
| 5,392,766 A | 2/1995 | Masterson et al. |
| 5,514,084 A | 5/1996 | Fisher |
| 6,447,446 B1 * | 9/2002 | Smith ................ A61B 1/00135 600/118 |

(Continued)

FOREIGN PATENT DOCUMENTS

| | | |
|---|---|---|
| DE | 102017107835 A1 | 10/2017 |
| JP | H04329510 A | 11/1992 |

(Continued)

OTHER PUBLICATIONS

English (Machine) translation of the Japanese reference No. 2007-117289 which reference was published on May 17, 2007.*

(Continued)

*Primary Examiner* — Thong Q Nguyen
(74) *Attorney, Agent, or Firm* — Carter, DeLuca & Farrell LLP

(57) ABSTRACT

An endoscope and lens cleaning device assembly includes a tubular body, a visualization device including a lens, and a lens cleaning device. The visualization device is supported on a distal portion of the tubular body. The lens cleaning device is supported on the distal portion of the tubular body and includes an iris mechanism having a plurality of vanes. The vanes are movable between a first position in which the vanes are positioned radially outwardly of the lens of the visualization device and a second position in which the vanes cover the lens of the visualization device. Each of the vanes has a cleaning surface that is positioned to contact the lens of the visualization device as the vanes move between the first and second positions to clean the lens of the visualization device.

12 Claims, 7 Drawing Sheets

(56) References Cited

U.S. PATENT DOCUMENTS

| | | | |
|---|---|---|---|
| 8,752,230 B2 | 6/2014 | Brand et al. | |
| 9,880,382 B1* | 1/2018 | Tippy | G03B 11/04 |
| 2007/0047188 A1* | 3/2007 | Kim | F16M 11/22 |
| | | | 248/371 |
| 2008/0108475 A1* | 5/2008 | Perng | B62M 6/55 |
| | | | 477/4 |
| 2009/0105543 A1 | 4/2009 | Miller et al. | |
| 2009/0209826 A1 | 8/2009 | Sanders et al. | |
| 2010/0136884 A1* | 6/2010 | Oh | B24B 49/16 |
| | | | 451/280 |
| 2013/0031735 A1 | 2/2013 | Brand et al. | |
| 2014/0094650 A1 | 4/2014 | Schaning | |

FOREIGN PATENT DOCUMENTS

| | | |
|---|---|---|
| JP | H0829699 A | 2/1996 |
| JP | H11287940 A | 10/1999 |
| JP | 2007117289 A | 5/2007 |

OTHER PUBLICATIONS

English (Machine) translation of the Japanese reference No. 11-287940 which reference was published on Oct. 19, 1999.*
European Office Action dated Jun. 12, 2020, issued in EP Appln. No. 19 153 696, 5 pages.
European Search Report dated Nov. 3, 2021, issued in corresponding EP Appln. No. 21180022, 7 pages.

* cited by examiner

ENDOSCOPE AND LENS CLEANING DEVICE ASSEMBLY

BACKGROUND

1. Technical Description

The present disclosure is directed to an endoscope and lens cleaning device assembly and, more particularly, to an endoscope including a lens cleaning device that is configured to clean a lens of the endoscope during an endoscopic surgical procedure at the surgical site.

2. Background of Related Art

During an endoscopic surgical procedure, surgical tools are inserted through small incisions in a patient to access an operative site within a body cavity. Typically, the body cavity is insufflated with an inert gas such as $CO_2$ and an endoscope is inserted through one of the small incisions to allow a clinician, e.g., a surgeon, to visualize the surgical site. Visualization of the surgical site is critical to successfully performing all surgical procedures.

During a surgical procedure, it is common for a lens of the endoscope to become smudged and/or obstructed with debris and require cleaning. Typically, the endoscope is removed from the body cavity and the lens of the endoscope is manually wiped clean. However, removal of the endoscope from the body cavity during the surgical procedure causes a temporary loss of visualization of the surgical site, increases the time required to perform the surgical procedure, and may result in a loss of insufflation within the body cavity.

A continuing need exists in the surgical arts for a method and device to clean the lens of an endoscope within a body cavity during a surgical procedure.

SUMMARY

One aspect of the disclosure is directed to an endoscope and lens cleaning device assembly including an endoscope having a tubular body, a visualization device including a lens supported on the endoscope, and a lens cleaning device. The tubular body defines a longitudinal axis and has a proximal portion and a distal portion. The visualization device is supported on the tubular body. The lens cleaning device is supported on the distal portion of the tubular body and includes an iris mechanism including a plurality of vanes. The vanes are movable between a first position in which the vanes are positioned radially outwardly of the lens of the visualization device and a second position in which the vanes cover the lens of the visualization device. Each of the vanes has a cleaning surface that is positioned to contact the lens of the visualization device as the vanes move between the first and second positions to clean the lens of the visualization device.

In embodiments, the lens cleaning device includes an actuator having a first end positioned adjacent the proximal end of the tubular body and a second end in contact with the iris mechanism, wherein the actuator is movable to cause movement of the vanes between the first and second positions.

In some embodiments, the actuator includes an actuator tube having a proximal portion, and a distal portion that supports at least a portion of the iris mechanism.

In certain embodiments, the proximal portion of the actuator tube includes a grip to facilitate movement of the actuator.

In embodiments, the actuator tube is rotatably supported in relation to the tubular body.

In some embodiments, the actuator tube is rotatably supported about the tubular body.

In certain embodiments, the iris mechanism further includes a support plate and an actuator ring, and the plurality of vanes is positioned between the support plate and the actuator ring.

In embodiments, the support plate is secured to the distal end of the tubular body.

In some embodiments, the actuator ring is secured to the distal portion of the actuator.

In certain embodiments, the actuator includes an actuator tube that is rotatably supported about the tubular body.

In embodiments, each of the plurality of vanes has a first end that is pivotably coupled to the support plate and a second end including a cam member.

In some embodiments, the actuator ring includes a plurality of cam channels, wherein each of the cam channels receives a respective one of the cam members of the plurality of vanes such that rotation of the actuator ring in relation to the support plate causes movement of the plurality of vanes between the first and second positions.

In certain embodiments, the tubular body defines a longitudinal bore that is dimensioned to receive a surgical device.

In embodiments, an irrigation channel is supported on the tubular body and has a distal end that is positioned to direct irrigation fluid onto the lens of the visualization device.

Another aspect of the present disclosure is directed to a lens cleaning device including an iris mechanism having a plurality of vanes, an actuator ring, and a support plate. The plurality of vanes is supported between the support plate and the actuator ring such that rotational movement of the actuator ring in relation to the support plate causes movement of the plurality of vanes between a first position in which the vanes define a central opening and a second position in which the vanes cover the central opening. Each of the vanes has a wiper surface that is positioned to contact a lens of a visualization device as the vanes move between the first and second positions to clean the lens of the visualization device.

BRIEF DESCRIPTION OF THE DRAWINGS

Various embodiments of the presently disclosed endoscope and lens cleaning device assembly are described herein below with reference to the drawings, wherein:

FIG. 4A is an enlarged view of the indicated area of detail shown in FIG. 1;

DETAILED DESCRIPTION OF EMBODIMENTS

Figure 1:
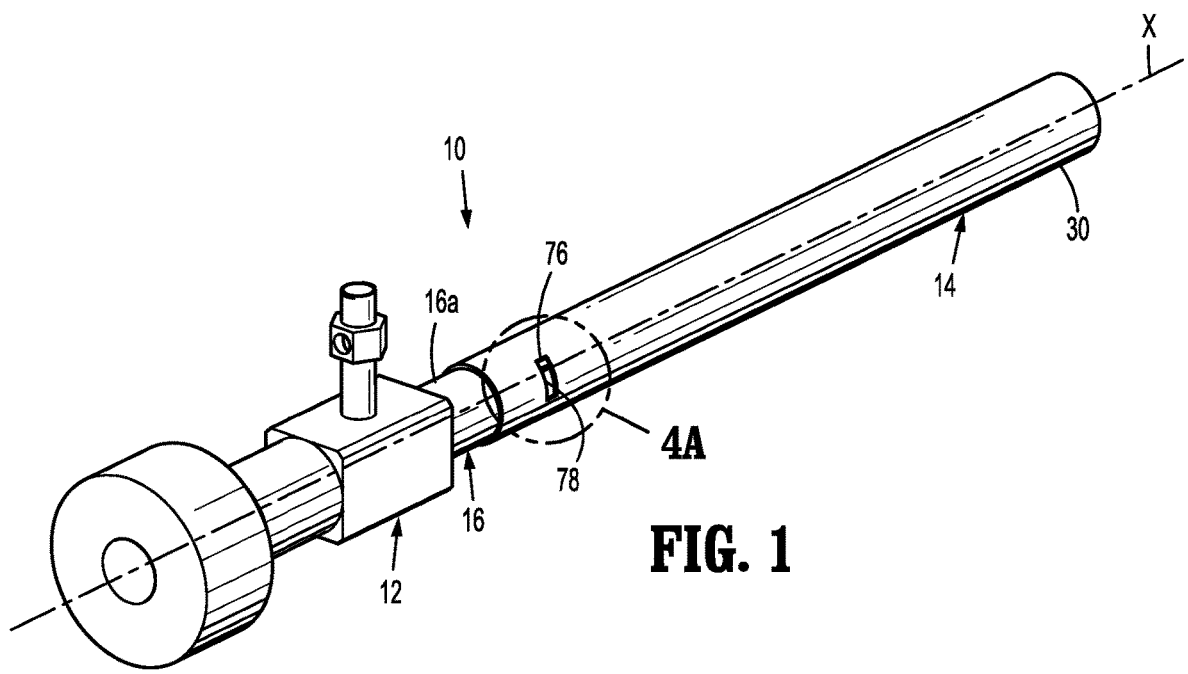
FIG. 1 is a side perspective view of an exemplary embodiment of the presently disclosed endoscope and lens cleaning device assembly.

The presently disclosed endoscope and lens cleaning device assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through a small diameter incision or trocar cannula assembly. In addition, the term "clinician" is used generally to refer to medical personnel including surgeons, doctors, nurses, and support personnel.

Figure 2:
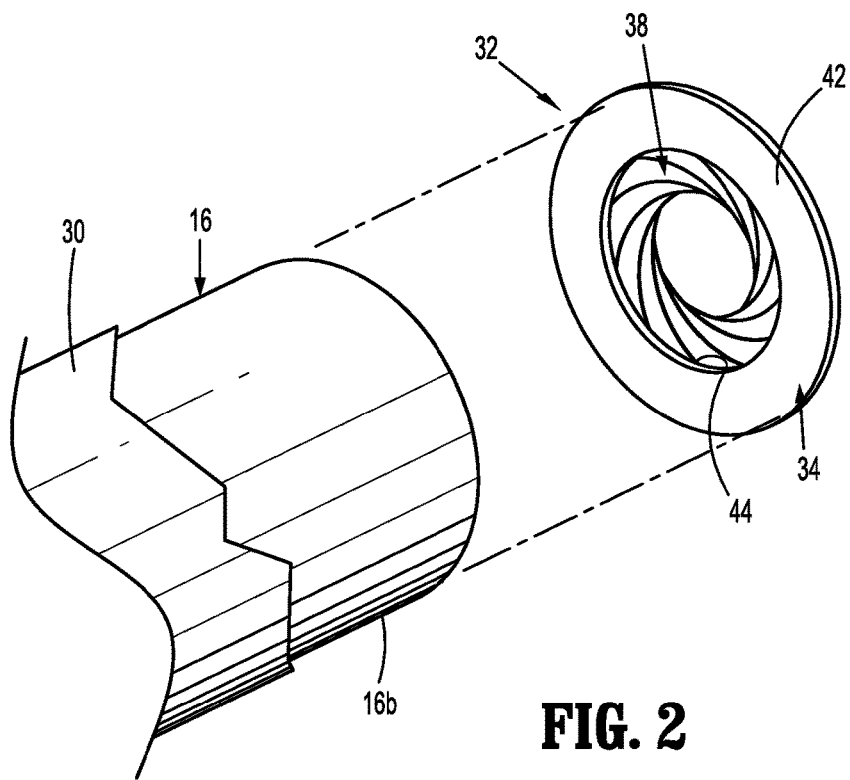
FIG. 2 is an enlarged view of a distal portion of the endoscope and lens cleaning device assembly shown in FIG. 1 with the lens cleaning device separated from a distal portion of the endoscope and a distal portion of an actuator of the lens cleaning device cutaway.

FIGS. 1 and 2 illustrate an exemplary embodiment of the presently disclosed endoscope and lens cleaning device assembly shown generally as assembly 10. The assembly 10 includes an endoscope 12 and a lens cleaning device 14. The endoscope 10 includes a tubular body 16 having a proximal portion 16a and a distal portion 16b. The tubular body 16 defines a longitudinal axis "X". The endoscope 12 includes a visualization device 20 including a lens 22 (FIG. 6A). The specifics of the endoscope 12 by itself do not define new features of the present disclosure. In fact, the presently disclosed lens cleaning device 14 can be incorporated onto any of a variety of different types of endoscopes that have a distally positioned lens. As such, specific details of the endoscope 12 will not be described in further detail herein.

Figure 3:
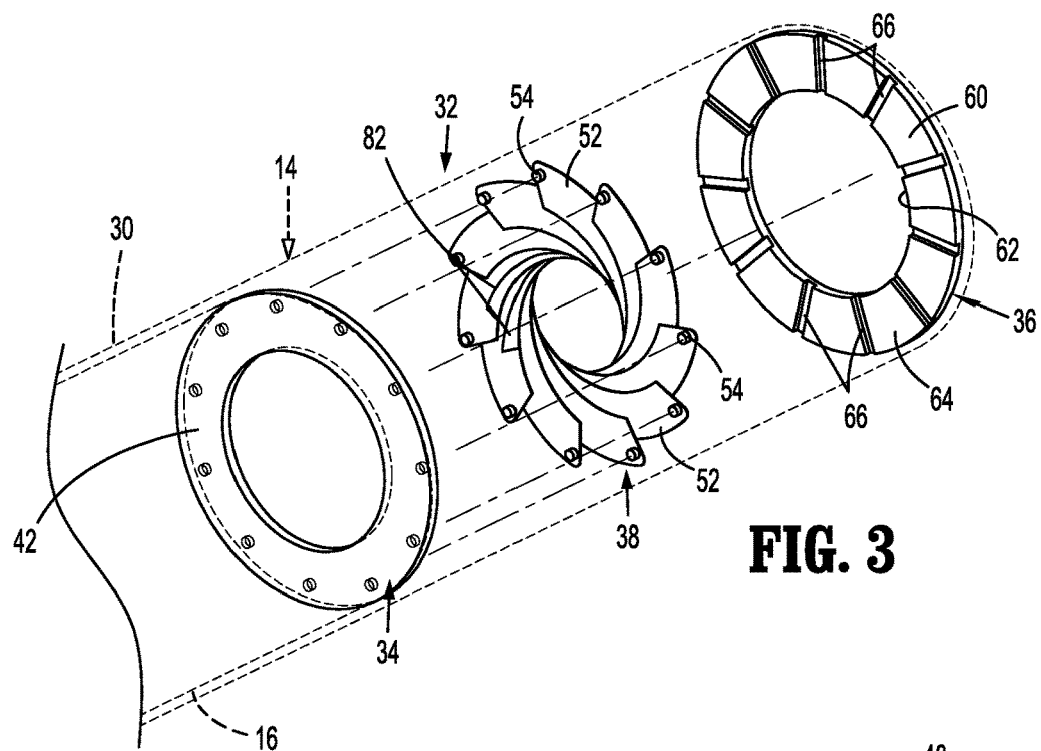
FIG. 3 is a side perspective, partially exploded view from the proximal end of the lens cleaning device shown in FIG. 3 with a distal portion of the actuator of the lens cleaning device and the endoscope shown in phantom.
Figure 4:
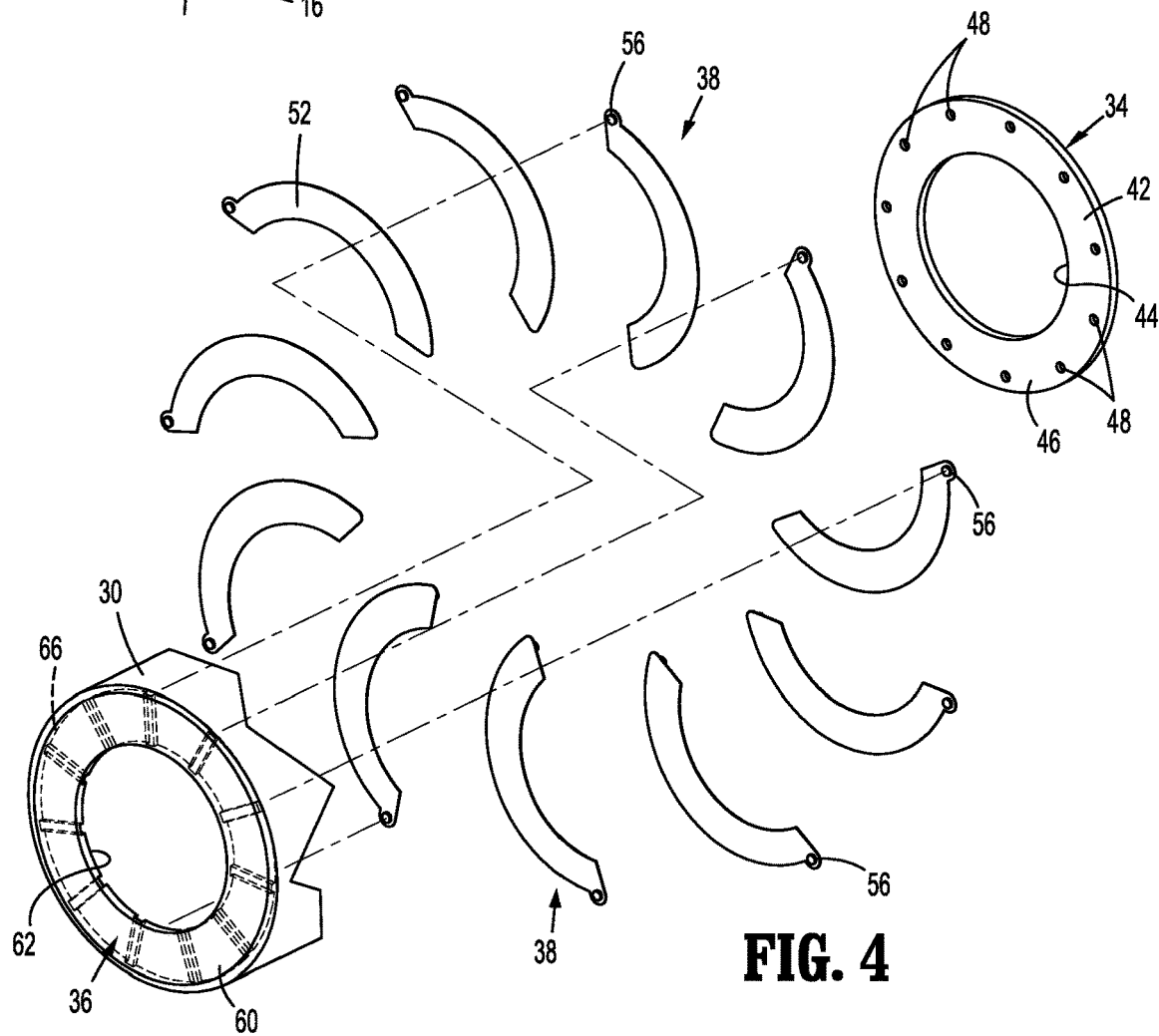
FIG. 4 is a side perspective, fully exploded view from the distal end of the lens cleaning device shown in FIG. 2 with the actuator cutaway.
Figure 5:
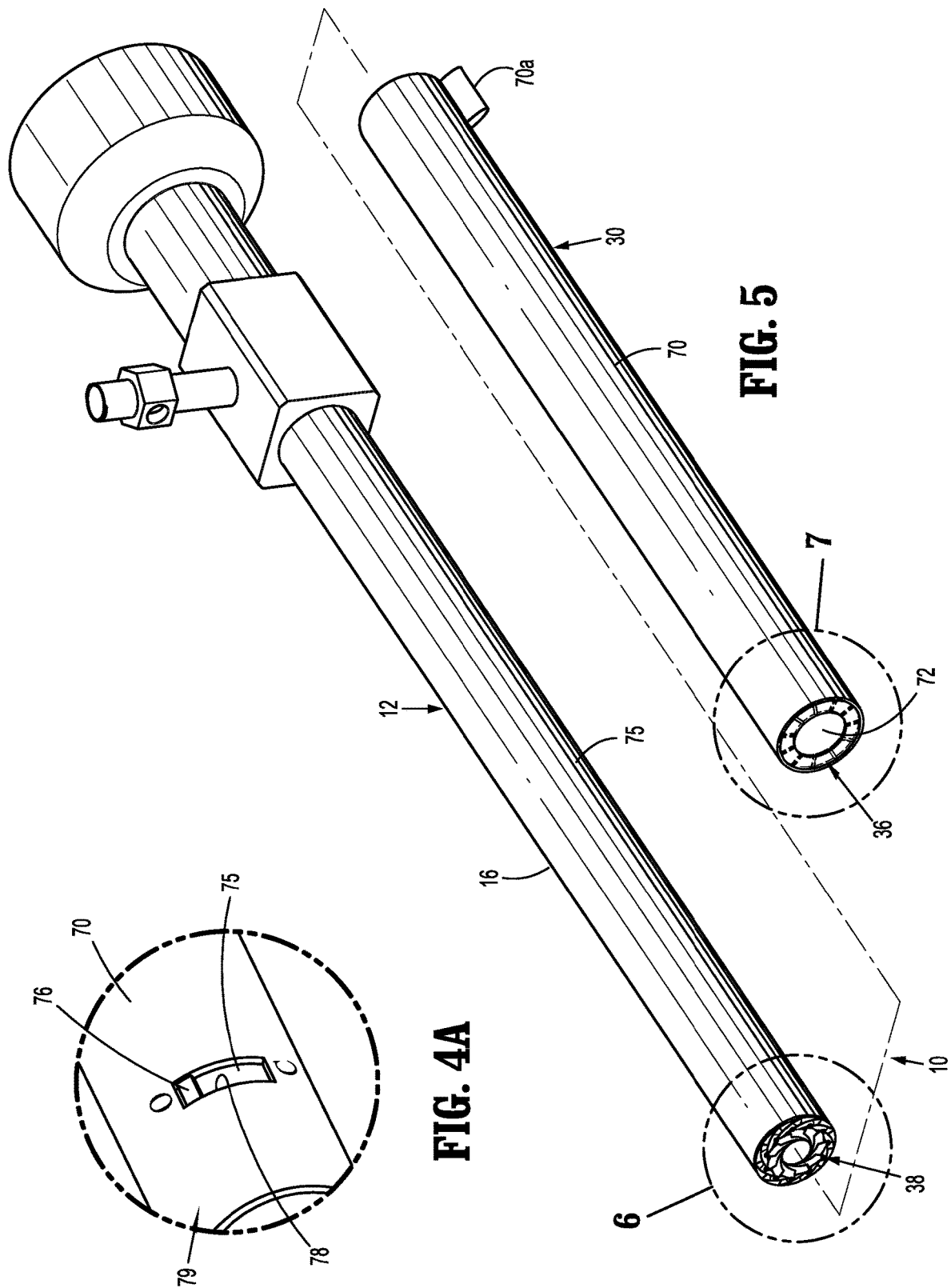
FIG. 5 is a side perspective view of the endoscope and lens cleaning device assembly shown in FIG. 1 with the actuator and actuator ring of the lens cleaning device separated from a tubular body of the endoscope.

Referring also to FIGS. 3 and 4, the lens cleaning device 14 includes an actuator 30 and an iris mechanism 32. The iris mechanism 32 includes a support plate 34, an actuator ring 36, and a plurality of vanes 38. The support plate 34 includes an annular body 42 defining a central opening 44. The annular body 42 has a distal face 46 that defines a plurality of openings 48 that are evenly spaced about the annular body 42.

Each of the vanes 38 includes a curved body 52 having a first end supporting a pivot member 54 (FIG. 3) and a second end supporting a cam member 56 (FIG. 4). The pivot members 54 of the vanes 38 extend proximally from the vanes 38 towards the support plate 34 and are received within the openings 48 of the support plate 34 such that the vanes 38 are pivotably supported on the support plate 34 and movable from a first open position (FIG. 9) spaced outwardly of the central opening 44 of the support plate 34 to a second closed position (FIG. 13) at least partially covering the central opening 44. The cam members 56 extend distally from the curved body 52 of the vanes 38 as described in further detail below.

The actuator ring 36 includes an annular body 60 defining a central opening 62. The annular body 60 has a proximal face 64 (FIG. 3) that defines a plurality of cam slots 66 that are evenly spaced about the annular body 60. Each of the cam slots 66 receives a respective one of the cam members 56 of the vanes 38. When the actuator ring 36 is rotated in relation to the support plate 34, the cam members 56 are forced to move through the cam slots 66 of the actuator ring 36 to move the vanes 38 between the first open position and the second closed position.

Referring to FIGS. 4A-7, in embodiments, the actuator 30 includes an actuator tube 70 that defines a longitudinal bore 72. The actuator tube may include a grip 70a to facilitate rotation of the actuator tube 70 and actuator ring 36 in relation to the support plate 34. The longitudinal bore 72 receives the tubular body 16 of the endoscope 12 such that the actuator tube 70 is rotatably supported about the tubular body 16. In some embodiments, the actuator ring 36 is supported on a distal portion of the actuator tube 70 and the support plate 34 is supported on the distal portion of the tubular body 16 of the endoscope 12 such that the vanes 38 are positioned between the support plate 34 and the actuator ring 36. When the actuator tube 70 is rotated in relation to the tubular body 16, the actuator ring 36 is rotated in relation to the support plate 34 to pivot the vanes 38 between their first and second positions.

In embodiments, the outer surface 75 (FIG. 4A) of the tubular body 16 of the endoscope 12 includes a raised surface or protrusion 76 and the actuator tube 70 includes an elongated slot 78 that receives the protrusion 76. The actuator tube 70 of the lens cleaning device 14 is rotatable about the tubular body 16 of the endoscope 12 to move the protrusion 76 within the slot 78. The ends of the slot 78 define the first and second positions of the vanes 38. An outer surface of the actuator tube 70 may include indicia 79 such as "O" for open and "C" (FIG. 4A) for closed to identify to a clinician when the iris mechanism 32 is in the open or closed position. Alternately, the indicia may include colors such as red and green or any other alpha-numeric indicia.

Referring again to FIG. 3, each of the vanes 38 of the iris mechanism 32 includes a proximally facing surface 80 that includes or supports a cleaning member 82 (FIG. 3) that is positioned to engage and wipe an outer surface of the lens 22 (FIG. 6A) when the vanes 38 are moved between the first and second positions. In embodiments, the cleaning member 82 may be in the form of a cloth or fabric attached to the vanes 38. Alternately, the use of other types cleaning members may be incorporated onto or impregnated into the vanes 38. Although not shown, the endoscope may include an irrigation supply to deliver fluid, e.g., to the saline to the lens 22 or cleaning member 82 to improve the cleaning capabilities of the lens cleaning device 14.

Figure 6:
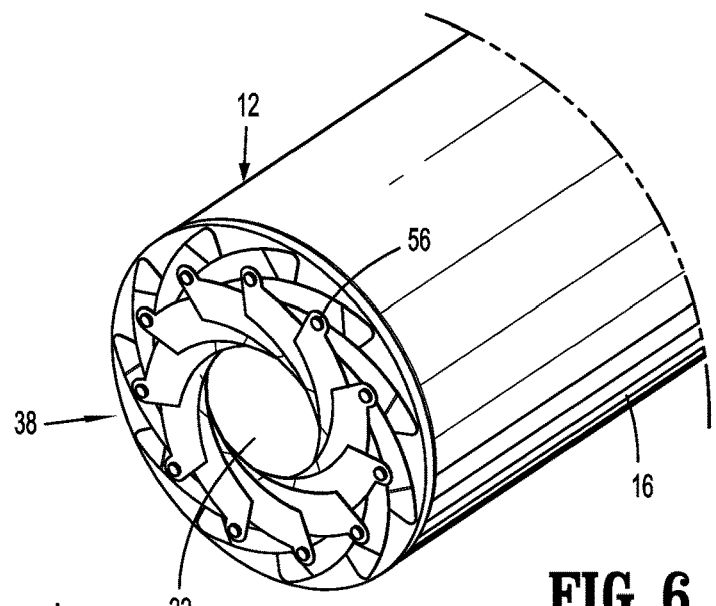
FIG. 6 is an enlarged view of the indicated area of detail shown in FIG. 3.
Figure 6A:
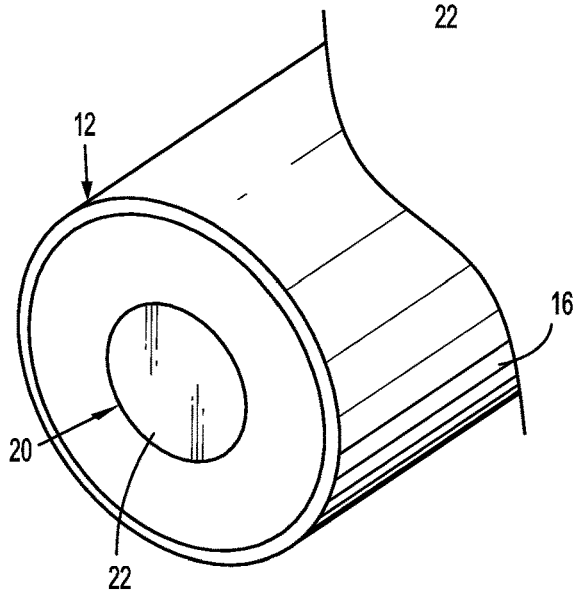
FIG. 6A is an enlarged view of a distal portion of the endoscope shown in FIG. 5.
Figure 7:
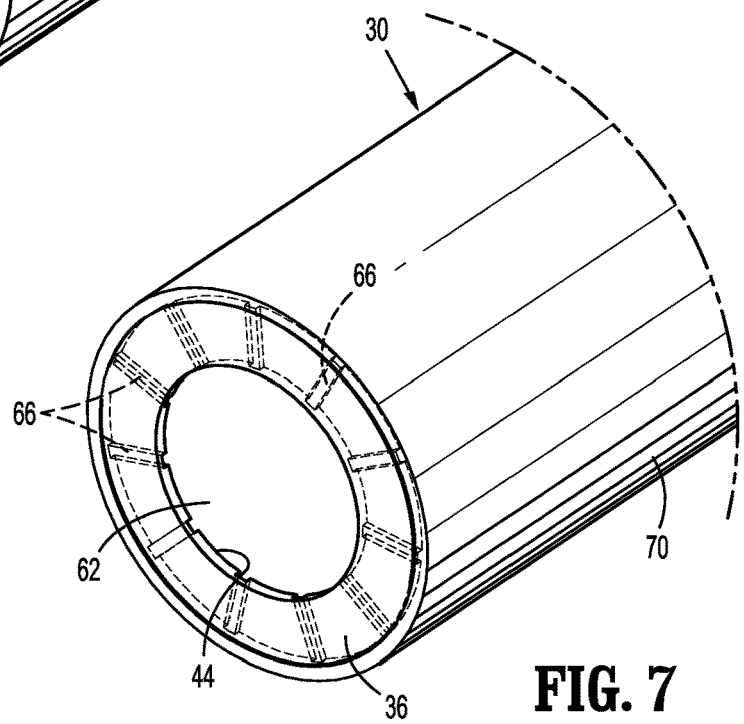
FIG. 7 is an enlarged view of the indicated area of detail shown in FIG. 5.
Figure 8:
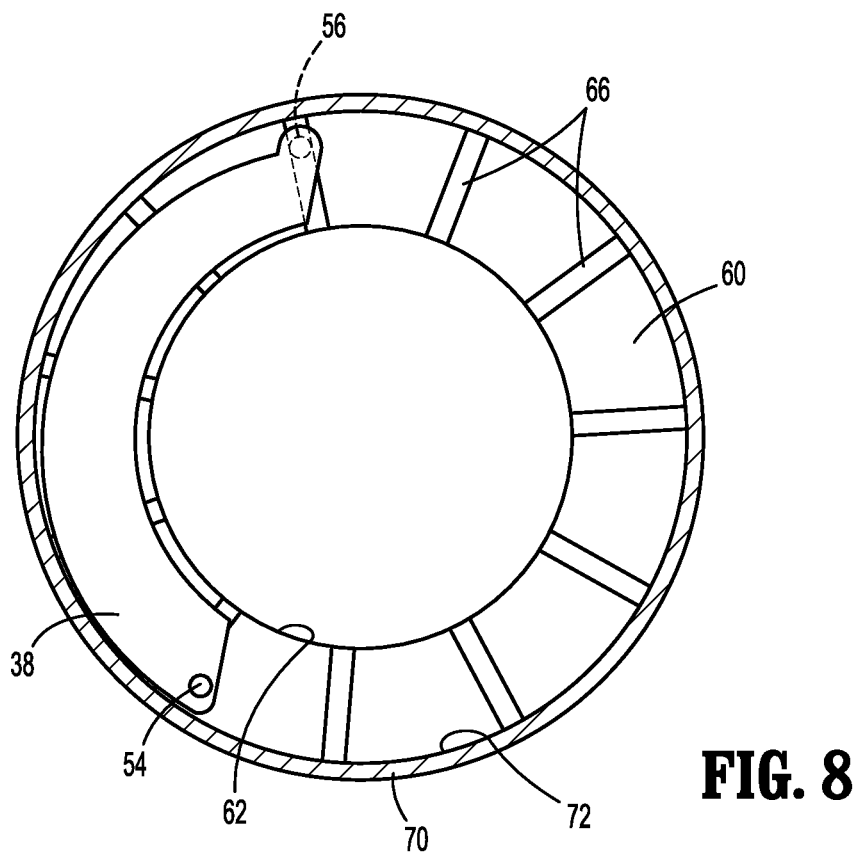
FIG. 8 is a cross-sectional view from the proximal end taken through the actuator and illustrating the support plate and one vane of an iris mechanism of the lens cleaning device shown in FIG. 2 in a first or open position.
Figure 9:
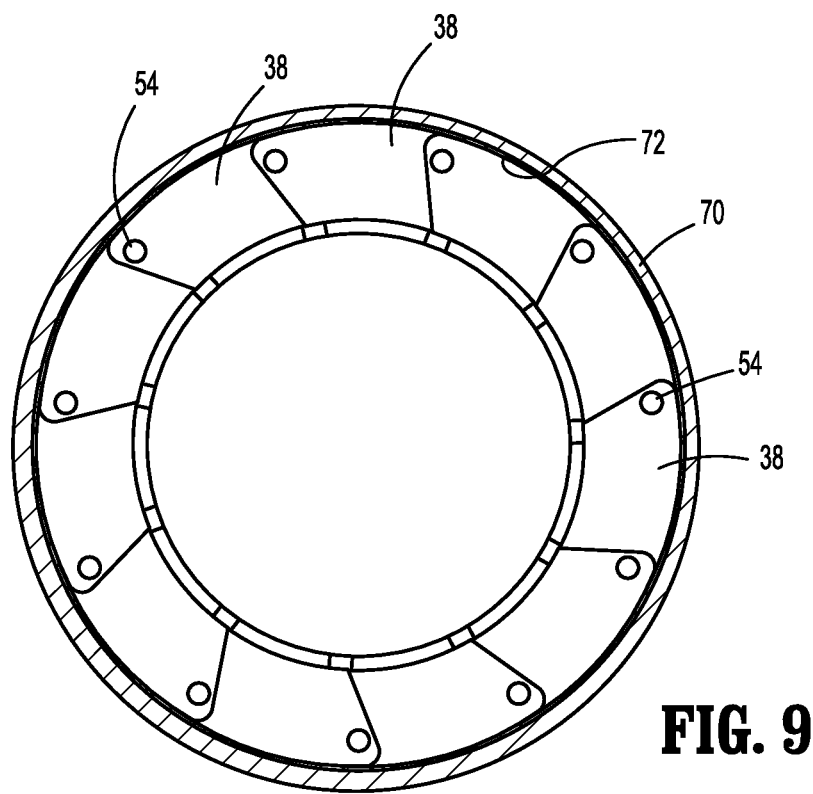
FIG. 9 is a cross-sectional view from the proximal end taken through the actuator of the lens cleaning device shown in FIG. 2 with the support plate removed and the vanes of the iris mechanism in the first position.

Referring to FIGS. 6, 8, and 9, when the vanes 38 are in the open position (FIG. 6), the vanes 38 are positioned outwardly of the lens 22 which is supported on the distal portion of the endoscope 12. Although shown to be centrally located on the endoscope 12, it is envisioned that the size and/or location of the lens 22 on the endoscope 12 may be varied as is known in the art. In the first or open position, the cam members 56 of the vanes 38 are positioned in an upper end of the cam slots 66 of the actuator ring 36 and the pivot members 54 are received in the openings 48 of the support plate 34.

Figure 10:
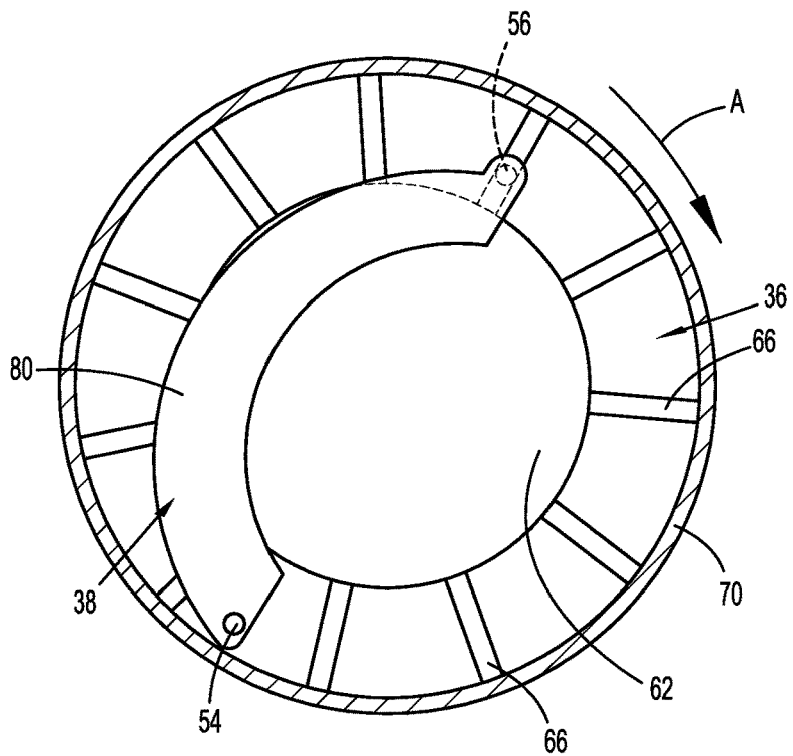
FIG. 10 is a cross-sectional view from the proximal end taken through the actuator and illustrating the support plate and one vane of the lens cleaning device shown in FIG. 2 moving towards a second or closed position.
Figure 11:
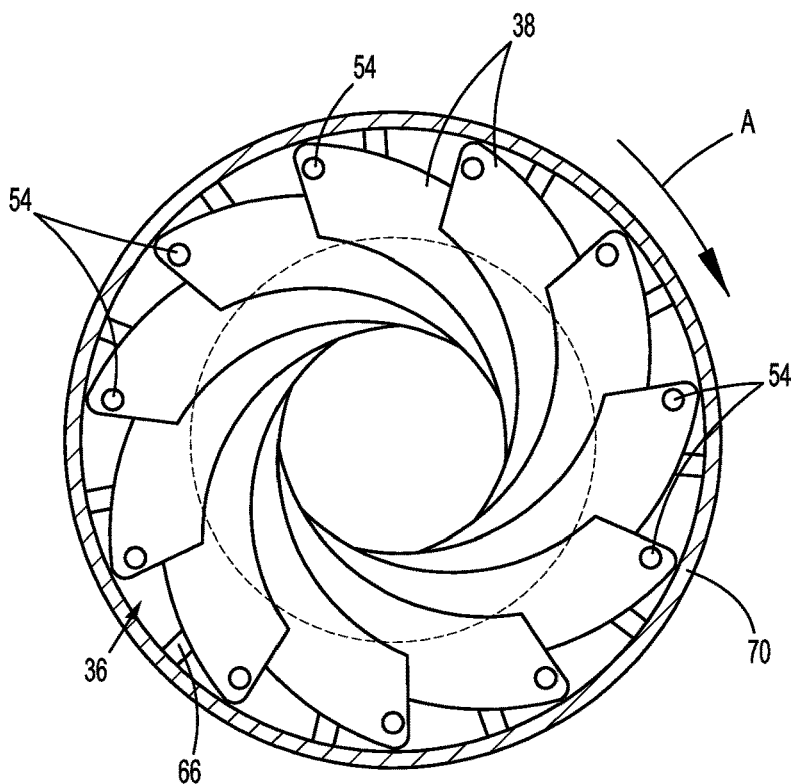
FIG. 11 is a cross-sectional view from the proximal end taken through the actuator of the lens cleaning device shown in FIG. 2 with the support plate removed and the vanes of the iris mechanism moving towards the second position.
Figure 12:
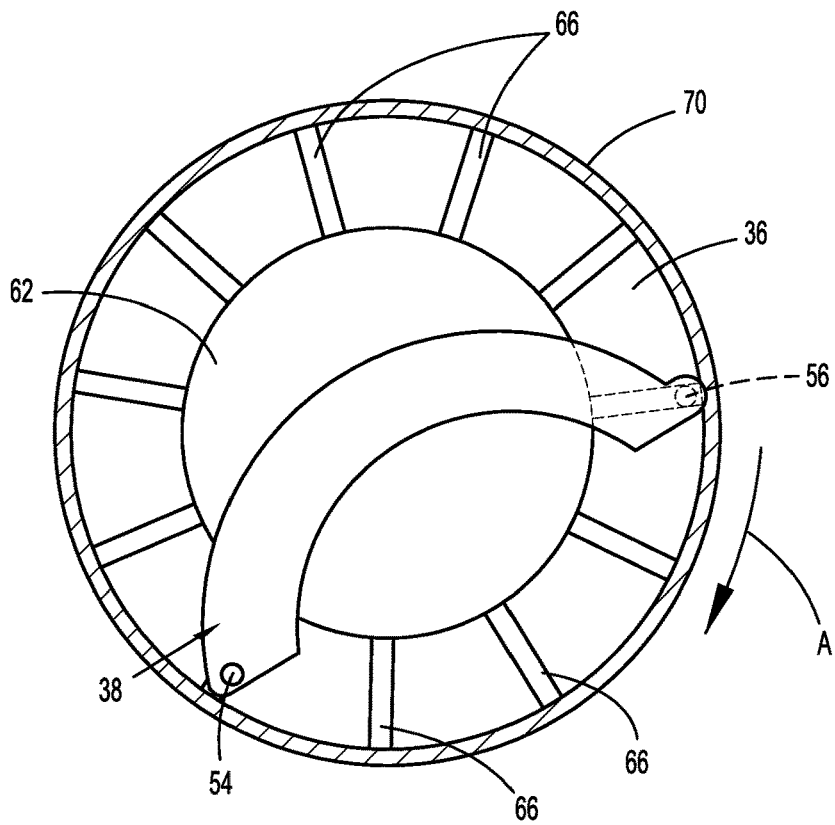
FIG. 12 is a cross-sectional view from the proximal end taken through the actuator and illustrating the support plate and one vane of the lens cleaning device shown in FIG. 2 in the second position.
Figure 13:
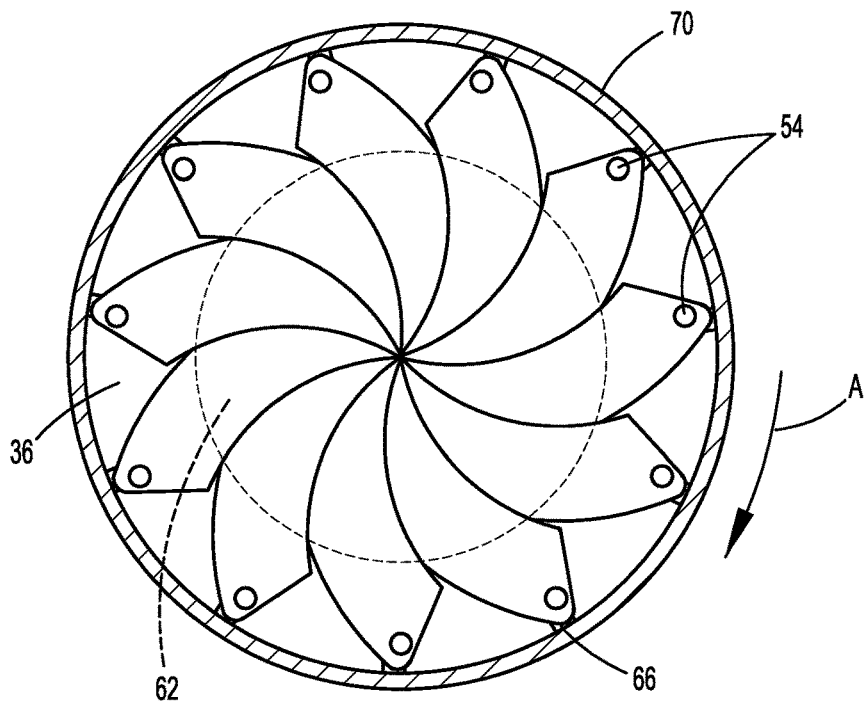
FIG. 13 is a cross-sectional view from the proximal end taken through the actuator of the lens cleaning device shown in FIG. 2 with the support plate removed and the vanes of the iris mechanism in the second position.

Referring to FIGS. 10 and 11, when the actuator tube 70 is rotated in relation to the endoscope 12 in the direction indicated by arrows "A", the actuator ring 36, which is secured to the distal portion of the actuator tube 70, rotates in relation to the support plate 34, which in some embodiments is supported on the distal portion of the tubular body 16 of the endoscope 12. As the actuator ring 36 rotates in relation to the support plate 34, since the pivot members 54 are radially fixed onto the support plate 34, the cam members 56 are initially moved within the cam slots 66 of the actuator ring 36 to pivot the vanes 38 inwardly across the central openings 44 and 62 of the support plate 34 and the actuator ring 36, respectively, and across the lens 22 of the endoscope 12. As seen in FIGS. 12 and 13, continued movement of the actuator tube 70 in the direction of arrows "A" moves the vanes 38 to the second or closed position in which the lens 22 is covered or substantially covered. The actuator tube 70 can be rotated in an opposite direction to move the iris mechanism 32 (FIG. 3) back to the open position.

Although the support plate is shown in a position secured to the distal portion of the tubular body of the endoscope 12, it is envisioned that the support plate 34 can be secured to the vanes 38 and the actuator ring 36 such that the lens cleaning device 14 forms an integral cleaning device. In such a device, a proximal face of the support plate 34 may include an adhesive that engage with a distal face of the endoscope 12 when the lens cleaning device 14 is supported about the endoscope 12 to prevent rotation of the support plate 34 in relation to the endoscope 12 when the actuator tube 70 is rotated in relation to the endoscope 12.

Although shown as a tubular member, the actuator 30 can be in the form of any structure or device that can affect rotation of the actuator ring 36 in relation to the support plate 34 to cause movement of the vanes 38 between the first and the second positions shown in FIGS. 11 and 13, respectively.

The presently disclosed endoscope lens cleaning device is configured for intraoperative use and facilitates cleaning of a lens of an endoscope without having to remove the endoscope from a body cavity. The endoscope is configured to be received through a small diameter trocar/cannula assembly, e.g. 5 mm or 10 mm trocar-cannula assembly.

During an endoscopic surgical procedure, the lens 22 (FIG. 6A) of the endoscope may require cleaning a number of times. This may be especially true during surgical procedures that require the use of electro-surgical instruments. The presently disclosed endoscope and lens cleaning device assembly 10 can remain within a body cavity during a surgical procedure to clean the lens of the endoscope 12 multiple times. This obviates the need to repeatedly remove the endoscope 12 from the body cavity to clean the endoscope. As described, removal of the endoscope from the body cavity for cleaning and subsequently reintroducing the endoscope to the body cavity may result in loss of insufflation gases, an increase in the chance of infection, an increase in the length of the surgical procedure, and repeated loss of visualization of the operative site.

Although not illustrated herein, the presently disclosed endoscope and lens cleaning device assembly may be supported on a robotic system such that the lens cleaning device can be robotically actuated.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An endoscope and lens cleaning device assembly comprising:
   an endoscope including:
      a tubular body having a proximal portion and a distal portion and defining a longitudinal axis; and
      a visualization device supported on the distal portion of the tubular body, the visualization device having a lens; and
   a lens cleaning device supported on the distal portion of the tubular body, the lens cleaning device including an iris mechanism including a plurality of vanes, an actuator ring, an actuator, and a support plate, the support plate defining a central opening, the vanes being supported between the support plate and the actuator ring such that rotational movement of the actuator ring in relation to the support plate causes movement of the plurality of vanes between a first position in which the vanes are positioned about the central opening of the support plate and a second position in which the vanes cover the central opening of the support plate, the actuator coupled to the actuator ring such that rotation of the actuator causes rotation of the actuator ring in relation to the support plate, the actuator including an actuator tube that is rotatable and defines a central bore dimensioned to receive the endoscope, wherein each of the vanes has a wiper surface that is positioned to contact the lens of the visualization device as the vanes move between the first and second positions to clean the lens of the visualization device.

2. The assembly of claim 1, wherein a proximal portion of the actuator tube includes a grip to facilitate movement of the actuator.

3. The assembly of claim 2, wherein the actuator tube is rotatably supported in relation to the tubular body.

4. The assembly of claim 3, wherein the actuator tube is rotatably supported about the tubular body.

5. The assembly of claim 1, wherein the support plate is secured to the distal portion of the tubular body.

6. The assembly of claim 5, wherein the actuator ring is secured to a second end of the actuator.

7. The assembly of claim 5, wherein each of the plurality of vanes has a first end that is pivotably coupled to the support plate and a second end including a cam member.

8. The assembly of claim 7, wherein the actuator ring includes a plurality of cam channels, each of the cam channels receiving a respective one of the cam members of the plurality of vanes such that rotation of the actuator ring in relation to the support plate causes movement of the plurality of vanes between the first and second positions.

9. A lens cleaning device comprising:
an iris mechanism including a plurality of vanes, an actuator ring, an actuator, and a support plate, the support plate defining a central opening, the vanes being supported between the support plate and the actuator ring such that rotational movement of the actuator ring in relation to the support plate causes movement of the plurality of vanes between a first position in which the vanes are positioned about the central opening of the support plate and a second position in which the vanes cover the central opening of the support plate, the actuator coupled to the actuator ring such that rotation of the actuator causes rotation of the actuator ring in relation to the support plate, the actuator including an actuator tube that is rotatable and defines a central bore dimensioned to receive an endoscope, wherein each of the vanes has a wiper surface that is positioned to contact a lens of a visualization device as the vanes move between the first and second positions to clean the lens of the visualization device.

10. The lens cleaning device of claim 9, wherein each of the plurality of vanes has a first end that is pivotably coupled to the support plate and a second end including a cam member.

11. The lens cleaning device of claim 10, wherein the actuator ring includes a plurality of cam channels, each of the cam channels receiving a respective one of the cam members of the plurality of vanes such that rotation of the actuator ring in relation to the support plate causes movement of the plurality of vanes between the first and second positions.

12. The lens cleaning device of claim 11, wherein the actuator ring is secured to a distal portion of the actuator.

\* \* \* \* \*